(12) United States Patent
Cornille et al.

(10) Patent No.: US 6,479,665 B2
(45) Date of Patent: Nov. 12, 2002

(54) PROCESS FOR THE PREPARATION OF N-CARBOXYANHYDRIDES

(75) Inventors: Fabrice Cornille, Bures sur Yvette (FR); Jean-Luc Copier, Arpajon (FR); Jean-Pierre Senet, Buthiers (FR); Yves Robin, Vert le Petit (FR)

(73) Assignee: Isochem, Paris Cedex (FR)

( * ) Notice: Subject to any disclaimer, the term of this patent is extended or adjusted under 35 U.S.C. 154(b) by 0 days.

(21) Appl. No.: 10/016,747

(22) Filed: Oct. 29, 2001

(65) Prior Publication Data

US 2002/0082431 A1 Jun. 27, 2002

(30) Foreign Application Priority Data

Oct. 30, 2000 (FR) .............................................. 00 13906

(51) Int. Cl.[7] ............................................. C07D 263/44
(52) U.S. Cl. ......................... 548/227; 548/229; 560/24
(58) Field of Search ................................. 548/227, 229

(56) References Cited

U.S. PATENT DOCUMENTS

| 3,369,026 A | | 2/1968 | Iwatsuki et al. ............ 260/307 |
| 3,658,831 A | | 4/1972 | Fujimoto et al. ........ 260/307 B |
| 4,496,541 A | * | 1/1985 | Huang et al. .................. 514/2 |
| 5,359,086 A | * | 10/1994 | Merslavic et al. .......... 548/233 |
| 6,262,274 B1 | * | 7/2001 | Chen et al. ................. 548/227 |

FOREIGN PATENT DOCUMENTS

| FR | 1561268 | 3/1969 |
| FR | 2000198 | 8/1969 |
| GB | 1189261 | 4/1970 |
| GB | 1210719 | 10/1970 |

* cited by examiner

Primary Examiner—Ceila Chang
Assistant Examiner—Kamal Saeed
(74) Attorney, Agent, or Firm—Bucknam & Archer

(57) ABSTRACT

The invention relates to a process for the preparation of N-carboxyanhydrides by reaction of the corresponding amino acid with phosgene, diphosgene and/or triphosgene in a solvent medium, characterized in that the reaction is a least partially carried out in the presence of an unsaturated organic compound which has one or more ethylenic double bonds, one of the carbon of at least one ethylenic double bond of which is completely substituted by substituents other than halogen atoms.

The N-carboxyanhydrides are thus obtained with better yields and an improved purity.

12 Claims, No Drawings

PROCESS FOR THE PREPARATION OF N-CARBOXYANHYDRIDES

The invention relates to an improved process for the preparation of N-carboxyanhydrides from the corresponding amino acids and phosgene, diphosgene or triphosgene.

N-Carboxyanhydrides (abbreviation NCA) obtained from α-, β- or γ-amino acids are very useful compounds due to the activation of their acid functional group. This is because they make possible the reaction of this acid functional group with any nucleophilic entity. Thus, the preparation of the amide functional group by reaction with an amine functional group is facilitated. For this reason, they readily polymerize and are used to form peptides. The ester bond is also easily formed by reaction with alcohol. They are also advantageous when it is desired to reduce an acid functional group.

Several processes are known for preparing N-carboxyanhydrides. One of the commonest and most direct is the process according to which an amino acid or its hydrochloride is reacted with phosgene, diphosgene or triphosgene in a solvent medium.

The general reaction diagram with phosgene is as follows:

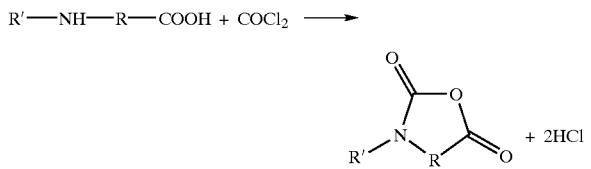

in which R represents the main radical of the α-, β- or γ-amino acid and R' represents a hydrogen atom or the radical of the secondary amino group of the amino acid, it being possible for R' to form a ring with R.

It is found that, in addition to the N-carboxyanhydride, a large amount of hydrochloric acid is also formed, that is to say 2 mol per mole of NCA. Hydrochloric acid is highly reactive. Its presence in the medium leads to side reactions and the appearance of chlorinated by-products. These chlorinated impurities, which remain in the NCAs produced, are entirely undesirable, both in terms of quality and in terms of yield. This is because they strongly interfere with the polymerization reaction of the NCAs. In order for this polymerization to be carried out suitably, it is necessary for the amount of chlorinated compounds present in the NCA monomers to be sufficiently low. Thus, the level of hydrolysable chlorine must generally be less than 0.05% by weight.

In point of fact, according to known processes, when the reaction is carried out without the presence of a basic compound, it is difficult to repeatably obtain such a low level of hydrolysable chlorine. On the other hand, when a basic compound is added to neutralize the hydrochloric acid, the polymerization of the NCAs, undesired at this stage, is activated and there is then the risk of it taking place in the medium.

Furthermore, one of the other difficulties of the prior processes is the choice of the solvent. This is because it has been found that, in solvents such as aliphatic esters, for example ethyl acetate, or non-polar aprotic solvents, for example dichloromethane or toluene, the reaction for the formation of the NCAs is generally very slow and incomplete. In a solvent from the family of the ethers, such as tetrahydrofuran or dioxane, the reaction is faster but these solvents are not completely inert with respect to phosgene and hydrochloric acid, which generates other impurities.

There consequently existed a need to improve the existing process in which the amino acid is reacted directly with phosgene, diphosgene or triphosgene, in order to obtain the NCAs with better yields and an improved purity, in particular having a level of hydrolysable chlorine of less than 0.05%. The decrease in the duration of the reaction, in the most inert solvents, was also highly desirable.

The process according to the present invention corresponds to these requirements. According to this process, N-carboxyanhydrides are prepared by reaction of the corresponding α-, β- or γ-amino acid or of one of its salts with phosgene, diphosgene and/or triphosgene in a solvent medium in the presence, during the entire or a portion of the duration of the reaction, of an unsaturated organic compound which has one or more double bonds of ethylenic type, the remainder of the molecule of which is inert with respect to compounds present in the medium and one of the carbons of at least one ethylenic double bond of which is completely substituted by substituents other than halogen atoms.

By virtue of this novel process, the problems which were posed in the prior art are solved. The hydrochloric acid which is given off becomes attached, as it is formed, to the ethylenic double bond or bonds of the unsaturated compound. The numerous side reactions brought about by hydrochloric acid are thus suppressed and, consequently, the appearance of the troublesome impurities also. Furthermore, the shifting of the reaction equilibrium in the direction of the production of the desired NCA is also promoted and, consequently, the kinetics of the reaction are accelerated.

It has also been found that, in the case of the conversion of amino acids with a secondary amine functional group, the presence of this unsaturated compound rendered pointless the addition, to the medium, of a tertiary amine, such as triethylamine or N-methylmorpholine. Such an amine was nevertheless, until now, regarded as necessary by a person skilled in the art in carrying out the cyclization starting from, as intermediate, the carbamoyl chloride which is first of all formed in the medium.

The process according to the invention makes it possible to obtain the N-carboxyanhydrides of the majority of cyclic or non-cyclic and natural or synthetic α-amino acids and their derivatives, the amine functional group of which is primary or secondary, and in particular of all those already known to react with phosgene, diphosgene and/or triphosgene.

Likewise, it is very useful for obtaining the N-carboxyanhydrides of β- and γ-amino acids and their derivatives comprising a primary or secondary amine functional group. This is because these compounds are regarded as difficult to prepare according to the prior processes.

The amino acids which are used as starting compounds are preferably α-, β- or γ-amino acids for which the α-, β- and γ carbon or carbons, if need be, situated between the reactive acid group and the reactive amino group, form a substituted or unsubstituted hydrocarbonaceous alkyl chain which can be included, in all or in part, in a substituted or unsubstituted and linear or branched alkyl radical and/or in a substituted or unsubstituted alkyl or heteroalkyl ring. The substituents are the groups or atoms which are usually found in amino acids, such as, for example, hydroxyl, carboxyl, mercapto, alkylthio, alkyldithio, alkyl, cycloalkyl, heterocycloalkyl, aryl, heteroaryl, alkyloxy or aryloxy groups, halogen atoms, such as fluorine, chlorine, bromine or iodine atoms, or amino, guanidino or amido groups which may or may not be substituted by alkyl groups.

More specifically, in the amino acids under consideration, the alkyl groups comprise from 1 to 7 carbon atoms and may or may not be substituted by the substituents indicated previously. The aryl groups are unsubstituted or substituted by substituents chosen from halogen atoms, such as fluorine, chlorine, bromine or iodine atoms, and alkyl, alkoxy, aryloxy, aryl, mercapto, alkylthio, hydroxyl, carboxyl, amino, alkylamino, dialkylamino, nitro or trifluoromethyl groups. When they are present, these substituent groups more particularly number from one to three. The aryl groups are in particular substituted or unsubstituted phenyl or naphthyl radicals.

The cycloalkyl groups are composed of rings having from 3 to 7 carbon atoms which are substituted or unsubstituted. The heterocycles, which may be substituted or unsubstituted, are cycloalkyl or aryl groups which comprise, in the ring, at least one heteroatom chosen from the nitrogen, oxygen or sulphur atom.

The substituents of the cycloalkyl or heterocycloalkyl groups are chosen from the substituents indicated previously for the alkyl and aryl radicals. The substituents of the heteroaryl groups are chosen from the substituents indicated for the aryl groups.

The heteroaryl groups are preferably substituted or unsubstituted 2- or 3-furanyl, 2- or 3-thienyl, 2-, 3- or 4-pyridinyl, 4-imidazolyl and 3-indolyl groups.

The amino acids can be in their various forms and, in particular when they have one or more asymmetric carbons, in their various enantiomeric forms, mixtures, either racemates or of diastereoisomers, or alternatively in the form of pure stereoisomers.

When the radical of the amino acid comprises functional groups, other than the amino group and the acid group which form the anhydride ring, capable of reacting under the conditions of the process, they are masked by protective groups in a known way.

Mention may be made, as examples of amino acids, of the commonest amino acids, such as glycine, alanine, valine, leucine, isoleucine, phenylalanine, serine, threonine, lysine, δ-hydroxylysine, arginine, ornithine, aspartic acid, asparagine, glutamic acid, glutamine, cysteine, cystine, methionine, tyrosine, thyroxine, proline, hydroxyproline, tryptophan, histidine and their derivatives.

The reactive amino group can be a primary or secondary amino group. Consequently, the nitrogen atom can carry a substituted or unsubstituted aliphatic, cycloaliphatic, araliphatic or aryl radical, as is usual for the class of the amines. In particular, this radical can be substituted by the groups indicated previously as substituents.

The radical of the amino group can also form an unsubstituted or substituted ring, as indicated above, with the remainder of the radical of the amino acid, such as, for example, in proline.

When the radical comprises reactive groups, they are protected conventionally.

Mention may in particular be made, as a radical of this amino group, of unsubstituted or substituted alkyl, cycloalkyl or aralkyl groups, for example substituted by groups as disclosed in U.S. Pat. No. 4,686,295 for the novel NCAs formed by means of phosgene and in particular substituted by one or more groups chosen from alkoxycarbonyl, aryloxycarbonyl and aralkyloxycarbonyl groups.

It is possible to use as starting compound, instead of the amino acid, one of its salts. The term "salts of the amino acid" is understood to mean the salts obtained by reaction of the amino group with organic or inorganic acids, such as, for example, sulphates, acetates, toluenesulphonates, methanesulphonates and, preferably, hydrohalides, in particular hydrochlorides and hydrobromides.

Hydrochlorides are the preferred salts.

The process is well suited to obtaining the N-carboxyanhydrides of amino acids such as N-(1-ethoxycarbonyl-3-phenylpropyl)alanine, leucine, alanine, N-(trifluoroacetyl)lysine, or the γ-benzyl ester or γ-methyl ester of glutamic acid.

For the implementation of the process, phosgene, diphosgene and/or triphosgene can be reacted with the amino acid to form the ring of the N-carboxyanhydride. Preferably, phosgene is used.

A large excess of phosgene with respect to the amino acid is not necessary. Thus, preferably, in the region of 1 to 2 mol of phosgene are added per mole of amino acid or of its salt.

Diphosgene or triphosgene are added in a corresponding amount in order to obtain the same phosgene/amino acid ratios.

The reaction can be carried out in an aprotic and polar solvent. Ethers, in particular tetrahydrofuran and dioxane, can be used but, preferably, the choice is made of a solvent belonging to the family of the aliphatic esters.

Aprotic and non-polar solvents belonging to the family of the chlorinated or non-chlorinated aliphatic and aromatic hydrocarbons, for example dichloromethane or toluene, can also be used.

Solvents belonging to the family of the esters or the hydrocarbons have the advantage of not reacting with phosgene or hydrochloric acid. Their use is consequently more advantageous.

Alkyl acetates are particularly well suited and especially ethyl acetate.

According to the invention, the presence in the reaction medium of an unsaturated organic compound having at least one ethylenic double bond, one of the carbons of at least one of these ethylenic double bond of which is completely substituted by substituents other than halogen atoms, is essential in obtaining NCAs with an improved purity and with better yields. Any compound which has at least one ethylenic double bond of this type to which hydrochloric acid can add can be used. This unsaturated compound must not, of course, comprise other groups and/or atoms, such as, especially the nitrile group and/or the halogen atoms, which can react with the other compounds present in the reaction medium. This would result in new impurities and falls in yield. If the compound comprises other reactive groups, they are protected in a known way.

Unsaturated compounds having a double bond, one of the carbons of which is completely substituted, are well suited.

Use is preferably made of a compound belonging to the family of the hydrocarbons. Mention may be made, as examples of such compounds, of α-pinene and diisobutene. α-Pinene is the preferred compound.

The amount of unsaturated compound which is used is generally from 1 to 3 mol per mole of amino acid or from 1.5 to 4 mol per mole of the salt of the amino acid, if this compound is chosen as starting compound, and, preferably, respectively n the region of 2 mol per mole of amino acid or in the region of 3 mol per mole of its salt.

The unsaturated compound can be present in the reaction medium from the beginning of the reaction but it can also be added during the reaction.

The reaction is generally carried out at the usual temperature of between 0° C. and 120° C. or equal to these values and preferably between approximately 40° C. and approximately 90° C.

The pressure under which the reaction is carried out is generally atmospheric pressure. The reaction can also be carried out under reduced pressure, in particular a pressure reduced to the region of 500 mbar, in particular in the region of 700 to 800 mbar.

The reaction is preferably carried out under anhydrous conditions.

One of the advantages of the process according to the invention is that the reaction duration is shortened and can even be decreased by half with respect to that of the prior art, in particular in solvents such as esters. Furthermore, as the latter solvents are cheaper, the implementation of the process according to the invention results in a real saving.

When the reaction is complete, the products are isolated according to the conventional procedure. Phosgene and the solvent are generally removed under the effect of reduced pressure. The chlorinated derivatives obtained from the unsaturated compounds are separated during the crystallization of the NCAs.

The NCA yields obtained after crystallization are markedly improved and often greater than 90%. The level of hydrolysable chlorine is always less than 0.05% and often the amount of chlorinated impurities is so low that this level cannot be accurately determined.

Consequently, the NCAs prepared according to the process described above can be used in numerous applications for which very pure products are required and in particular for the preparation of pharmaceutical products.

The examples which follow illustrate the invention without, however, limiting it.

EXAMPLE 1

Preparation of the N-carboxyanhydride of leucine (H-Leu-NCA)

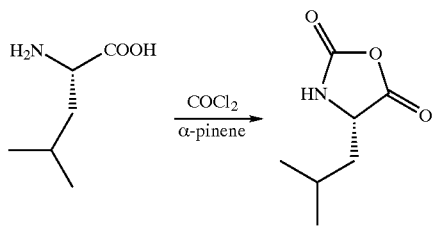

1 liter of ethyl acetate and then 100 g of L-leucine (0.76 mol, 1 equivalent) are added to a thermostatically-controlled 2.5 liter reactor rendered inert beforehand with nitrogen. 208.0 g of α-pinene (1.52 mol, 2 equivalents) are introduced into this mechanically stirred suspension and the mixture is cooled to 5° C. 154.5 g of phosgene (1.56 mol, 2.05 equivalents) are then introduced into this reaction medium by bubbling over one hour while maintaining the temperature between 5° C. and 10° C. The reaction medium is subsequently heated to 60°–65° C. After a stationary phase of two hours at this temperature, the reaction medium is degassed under reduced pressure in order to remove the excess phosgene and in order to concentrate it by removing all the ethyl acetate.

750 ml of industrial-grade heptane are subsequently added under warm conditions to the concentrated medium. The H-Leu-NCA begins to crystallize. The reaction medium is then cooled to 0°–5° C. Filtration is carried out under a nitrogen atmosphere. After drying under vacuum at ambient temperature, 101.9 g (yield: 85%) of L-H-Leu-NCA are obtained, the purity of which is greater than 99.9% (determined by HPLC) and the level of hydrolysable chlorine of which, determined by the argentometric method, is 0.018% by weight.

EXAMPLE 2

Preparation of the N-carboxyanhydride of alanine (H-Ala-NCA)

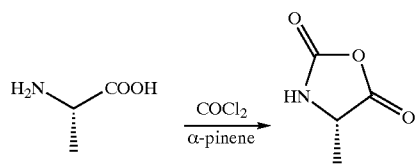

125 g of alanine (H-Ala-OH) (1.4 mol) are suspended in a mixture of 445 ml of α-pinene (382 g, 2.8 mol, 2 eq.) and 937 ml of ethyl acetate. The suspension is brought to reflux and 209 g (2.11 mol, 1.5 eq.) of gaseous phosgene are introduced. After a stationary phase of 12 hours, a few insoluble parts remain.

Distillation is carried out in order to separate, from the reaction medium, 800 ml of a mixture of ethyl acetate and phosgene and then the remaining medium is filtered under warm conditions.

800 ml of industrial-grade heptane are added under warm conditions to the concentrated medium and the mixture is cooled to −10° C. overnight. The product which crystallized is filtered off and washed with industrial-grade heptane.

After drying, 111 g of H-Ala-NCA are obtained, i.e. a yield of 68.8%. The amount of hydrolysable chlorine is too low to be determined as it is less than the detection limit, that is to say less than 0.01%.

EXAMPLE 3

Preparation of the N-carboxyanhydride of N-(trifluoro-acetyl)lysine (H-Lys(TFA)-NCA)

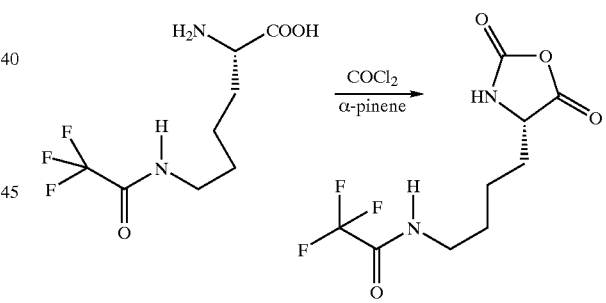

250 g of H-TFA-Lys-OH (1.03 mol) are suspended in a mixture of 328 ml of α-pinene (281 g, 2.06 mol, 2 eq.) and 1 875 ml of ethyl acetate. The suspension is heated to 65° C. and then 154 g (1.55 mol, 1.5 eq.) of gaseous phosgene are introduced. The reaction medium is brought to reflux and is left under stationary conditions for 3 hours.

Distillation is carried out in order to separate 1 750 ml of a mixture of ethyl acetate and of phosgene. 1 750 ml of industrial-grade heptane are added under warm conditions to the remaining medium and the mixture is cooled to −10° C. overnight. The product which crystallized is separated by filtration and washed with industrial-grade heptane.

After drying, 261 g of H-Lys(TFA)-NCA are obtained, i.e. a yield of 94.48%. The amount of hydrolysable chlorine is too low to be determined as it is less than the detection limit, that is to say less than 0.01%.

EXAMPLE 4

Preparation of the N-carboxyanhydride of the γ-benzyl ester of glutamic acid (H-Glu(Obzl)-NCA)

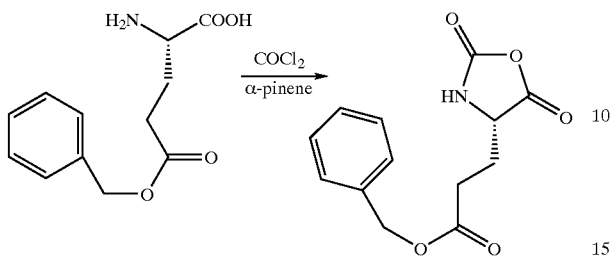

250 g of H-Glu(OBzl)—OH (1.05 mol) are suspended in a mixture of 334 ml of α-pinene (287 g, 2.1 mol, 2 eq.) and 1 875 ml of ethyl acetate. The suspension is cooled to +5° C. and then 164 g (2.28 mol, 1.57 eq.) of gaseous phosgene are introduced. The reaction medium is heated to reflux and is left under stationary conditions at this temperature for 3 hours.

Distillation is subsequently carried out in order to separate 1 500 ml of a mixture of ethyl acetate and of phosgene. 1 500 ml of industrial-grade heptane are added under warm conditions to the remaining medium and the mixture is cooled to −10° C. over 2 hours. The product which crystallized is separated by filtration and washed with industrial-grade heptane.

After drying, 253 g of H-Glu(OBzl)-NCA are obtained, i.e. a yield of 91.3%. The level of hydrolysable chlorine cannot be determined as it is less than 0.01% (detection limit of the method).

Comparative Example

Preparation of the N-carboxyanhydride of the γ-benzyl ester of glutamic acid (H-Glu(OBzl)-NCA)

100 g of H-Glu(OBzl)—OH (0.42 mol) are suspended in 885 ml of ethyl acetate. The suspension is cooled to +5° C. and then 90 g (0.91 mol, 2.16 eq.) of gaseous phosgene are introduced.

The reaction medium is brought to reflux. Despite the presence of a greater excess of phosgene in comparison with the preceding example, the reaction is slow and it is necessary to leave the reaction medium under stationary conditions at the reflux temperature for 6 hours instead of 3 hours, as in the preceding example.

Distillation is subsequently carried out in order to separate 600 ml of a mixture of ethyl acetate and of phosgene. 600 ml of industrial-grade heptane are added under warm conditions and the mixture is cooled to −10° C. over 2 hours. The crystallized product is separated by filtration and washed with industrial-grade heptane.

After drying, 88 g of H-Glu(OBzl)-NCA are obtained, i.e. a yield of 74.6%. The level of hydrolysable chlorine is 0.13%.

EXAMPLE 5

Preparation of the N-carboxyanhydride of the γ-methyl ester of glutamic acid (H-Glu(OMe)-NCA)

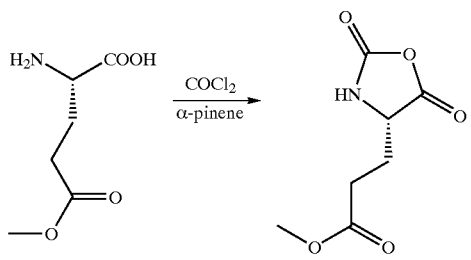

250 g of H-Glu(OMe)—OH (1.55 mol) are suspended in a mixture of 493 ml of α-pinene (423 g, 3.1 mol, 2 eq.) and 1 875 ml of ethyl acetate. The suspension is heated to 65° C. and then 227 g (2.31 mol, 1.5 eq.) of gaseous phosgene are introduced.

The reaction medium is brought to reflux and is left under stationary conditions for 6 hours. Distillation is subsequently carried out in order to separate 1 500 ml of a mixture of ethyl acetate and of phosgene.

1 500 ml of industrial-grade heptane are added under warm conditions to the remaining medium and the medium is cooled to −10° C. overnight. The product which crystallized is separated by filtration and washed with industrial-grade heptane.

After drying, 269 g of H-Glu(OMe)-NCA are obtained, i.e. a yield of 92.6%. The level of hydrolysable chlorine is less than 0.01% (detection limit).

EXAMPLE 6

Preparation of the N-carboxyanhydride of N-(1-ethoxy-carbonyl-3-phenylpropyl) alanine (EPAL-NCA)

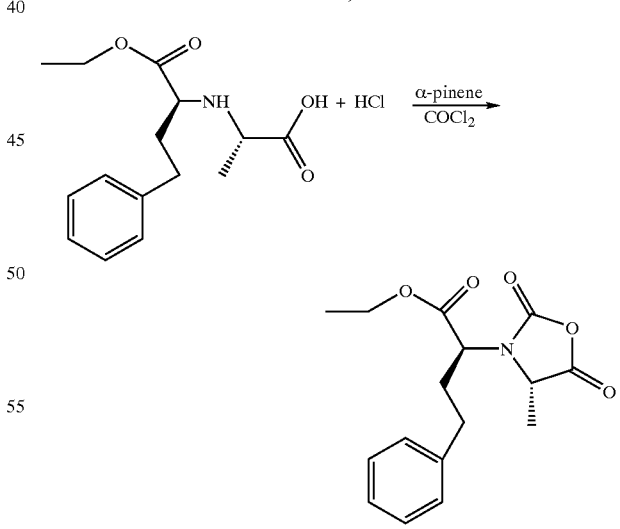

2.6 liters of anhydrous ethyl acetate and then 312 g of EPAL (1.11 mol, 1 equivalent) are added to a thermostatically-controlled 3 liter reactor rendered inert beforehand with nitrogen. 45 g of gaseous HCl (1.22 mol, 1.1 equivalent/EPAL) are then introduced over 15 minutes at 40° C. into this mechanically stirred suspension.

223 g of gaseous phosgene (2.22 mol, 2.00 eq.) are subsequently introduced into the reaction medium over one hour. The reaction medium is subsequently heated to 60°–65° C. After a stationary phase of two hours at this temperature, 227 g of α-pinene (1.66 mol, 1.5 eq./EPAL) are introduced. After an additional stationary phase of 30 minutes, the reaction medium is degassed under reduced pressure to remove the excess phosgene and to separate all the ethyl acetate.

1 385 ml of isopropyl ether are then added to the concentrated reaction medium. The medium is cooled to 0°–5° C. and the crystallization of the EPAL-NCA is observed. It is separated by filtration under a nitrogen atmosphere.

After drying under vacuum at ambient temperature, 312 g (yield: 91.5%) of EPAL-NCA (white solid) are obtained, the purity of which is greater than 99.7% (determined by HPLC) and the level of hydrolysable chlorine of which is 0.04%.

What Is Claimed Is:

1. Process for the preparation of N-carboxyanhydrides by reaction of the corresponding α-, β- or γ-amino acid or of one of its salts with phosgene, diphosgene and/or triphosgene in a solvent medium, wherein the reaction is at least during a portion of its duration carried out in the presence of an unsaturated organic compound which has one or more ethylenic double bonds, the remainder of the molecule of which is inert with respect to compounds present in the medium and one of the carbons of at least one ethylenic double bond of which is completely substituted by substituents other than halogen atoms.

2. Process according to claim 1, wherein the amino acid is reacted with phosgene.

3. Process according to claim 1, wherein the unsaturated organic compound is chosen from hydrocarbons.

4. Process according to claim 1, wherein the unsaturated organic compound is α-pinene.

5. Process according to claim 1, wherein the amount of the unsaturated organic compound used is from 1 to 3 mol per mole of the amino acid or from 1.5 to 4 mol per mole of the salt of the amino acid.

6. Process according to claim 1, wherein the solvent is chosen from aliphatic esters and chlorinated or non-chlorinated aliphatic esters and chlorinated or non-chlorinated aliphatic or aromatic hydrocarbons.

7. Process according to claim 6, wherein the solvent is ethyl acetate.

8. Process according to claim 1, wherein the reactive amino group of the amino acid is primary or secondary.

9. Process according to claim 1, wherein when the amino acid comprises reactive groups, other than the acid group which form the anhydride, they are protected.

10. Process according to claim 1, wherein the starting amino acid is leucine, alanine, N-(trifluoroacetyl)lysine, the γ-benzyl ester or γ-methyl ester of glutamic acid, or N-(1-ethoxycarbonyl-3-phenylpropyl) alanine, or one of their salts.

11. Process according to claim 1, wherein the salt of the amino acid is a sulphate, an acetate, a toluenesulphonate or a methanesulphonate.

12. Process according to claim 1, wherein the salt of the amino acid is a hydrohalide.

* * * * *